United States Patent
Bathe et al.

(10) Patent No.: US 7,037,689 B2
(45) Date of Patent: May 2, 2006

(54) METHODS FOR PRODUCING AMINO ACIDS IN CORYNEFORM BACTERIA USING AN ENHANCED SIGC GENE

(75) Inventors: Brigitte Bathe, Salzkotten (DE); Stephan Hans, Osnabrück (DE); Mike Farwick, Bielefeld (DE); Thomas Hermann, Bielefeld (DE); Walter Pfefferle, Halle (DE)

(73) Assignee: Degussa AG, Düsseldorf (DE)

( * ) Notice: Subject to any disclaimer, the term of this patent is extended or adjusted under 35 U.S.C. 154(b) by 280 days.

(21) Appl. No.: 09/941,936

(22) Filed: Aug. 30, 2001

(65) Prior Publication Data

US 2002/0146782 A1     Oct. 10, 2002

(30) Foreign Application Priority Data

| Sep. 2, 2000 | (DE) | ................................. 100 43 332 |
| Jul. 10, 2001 | (DE) | ................................. 101 33 426 |

(51) Int. Cl.
*C12P 13/04*     (2006.01)

(52) U.S. Cl. .................. 435/106; 435/115; 435/252.32
(58) Field of Classification Search .................... 435/6, 435/106, 115, 252.32
See application file for complete search history.

(56) References Cited

FOREIGN PATENT DOCUMENTS

| EP | 0 864 654 | 9/1998 |
| EP | 0864654 A1 * | 9/1998 |
| EP | 1 006 192 | 6/2000 |
| EP | 1 108 790 A2 | 6/2001 |
| WO | WO 01/000804 | 1/2001 |

OTHER PUBLICATIONS

Amador et al. Strucuture and organization of the rrnD operon of *Brevibacterium lactofermentum*: analysis of the 16S rRNA gene. Microbiology (1999) 145:915-924.*

Oguiza J A et al., "Multiple Sigma Factor Genes in *Brevibacterium lactofermentum*: Characterization of sigA and sigB" Journal of Bacteriology, Washington, DC, US, vol. 178, No. 2, Jan. 1996, pp. 550-553, abstract.

* cited by examiner

*Primary Examiner*—Kathleen Kerr
(74) *Attorney, Agent, or Firm*—Smith, Gambrell & Russell, L.L.P.

(57) ABSTRACT

The invention relates to an isolated polynucleotide having a polynucleotide sequence which codes for the sigC gene from *Corynebacterium glutamicum*, and a host-vector system having a coryneform host bacterium, such as *Corynebacterium glutamicum*, and a vector which carries at least the sigC gene according to SEQ ID No 1, and the use of polynucleotides which comprise the sequences according to the invention as hybridization probes.

15 Claims, 2 Drawing Sheets

Fig. 1: Map of the plasmid pEC-XK99E
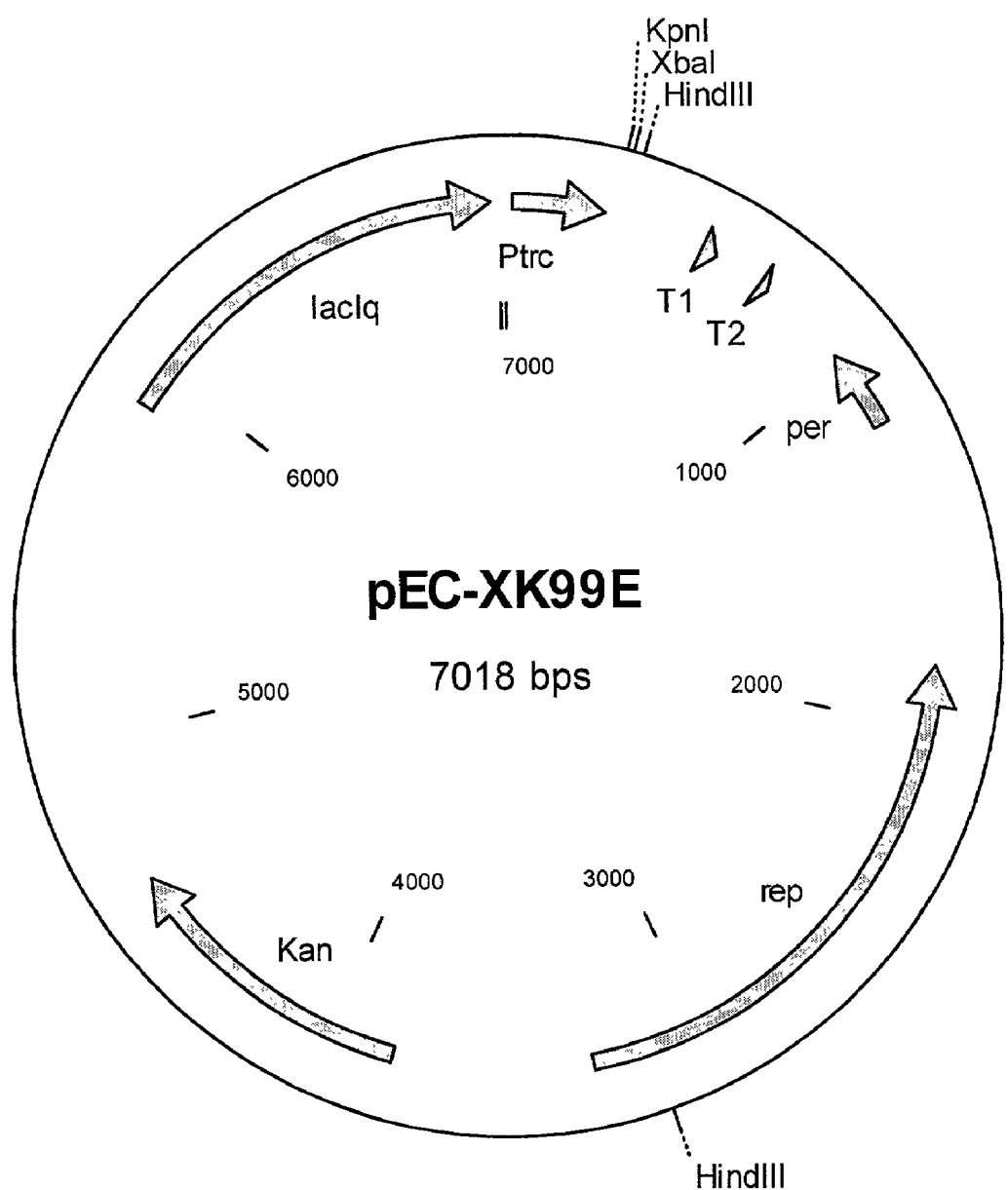

Fig. 2: Plasmid pEC-XK99EsigCb2ex
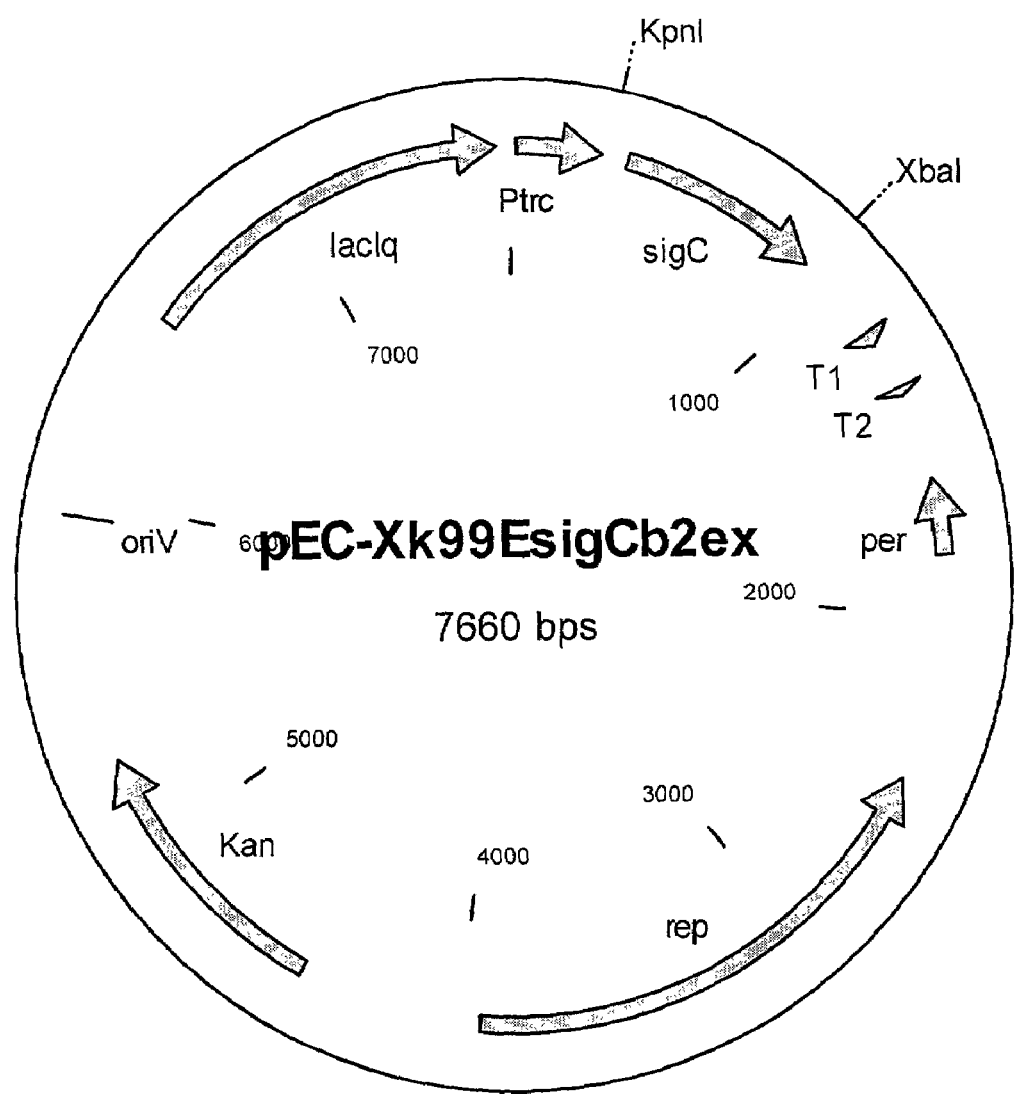

METHODS FOR PRODUCING AMINO ACIDS IN CORYNEFORM BACTERIA USING AN ENHANCED SIGC GENE

BACKGROUND OF THE INVENTION

The subject of the present invention are nucleotide sequences of coryneform bacteria coding for the sigC gene and a process for the enzymatic production of amino acids using bacteria in which the sigC gene is enhanced. All references cited herein are expressly incorporated by reference. Incorporation by reference is also designated by the term "I.B.R." following any citation.

L-amino acids are used in human medicine and in the pharmaceutical industry, in the foodstuffs industry and, most especially, in animal nutrition.

It is known that amino acids can be produced by fermentation of strains of coryneform bacteria, in particular *Corynebacterium glutamicum*. On account of the great importance of amino acids efforts are constantly being made to improve the production processes. Process improvements may involve fermentation technology measures such as for example stirring and provision of oxygen, or the composition of the nutrient media, such as for example the sugar concentration during the fermentation, or the working-up to the product form by for example ion exchange chromatography or the intrinsic performance properties of the microorganism itself.

In order to improve the performance properties of these microorganisms methods involving mutagenesis, selection and mutant selection are employed. In this way strains are obtained that are resistant to antimetabolites or are auxotrophic for regulatory important metabolites, and that produce amino acids.

For some years methods of recombinant DNA technology have also been used to improve L-amino acid-producing strains of *corynebacterium*, by amplifying individual amino acid biosynthesis genes and investigating the effect on amino acid production.

The invention provides new techniques for the improved enzymatic production of amino acids.

BRIEF SUMMARY OF THE INVENTION

When L-amino acids or amino acids are mentioned hereinafter, it is understood that this refers to one or more amino acids including their salts, selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. Lysine is particularly preferred.

The present invention provides an isolated polynucleotide from coryneform bacteria containing a polynucleotide sequence coding for the sigC gene, selected from the group a) polynucleotide that is at least 70% identical to a polynucleotide coding for a polypeptide that contains the amino acid sequence of SEQ ID No. 2,
b) polynucleotide coding for a polypeptide that contains an amino acid sequence that is at least 70% identical to the amino acid sequence of SEQ ID No. 2,
c) polynucleotide that is complementary to the polynucleotides of a) or b), and
d) polynucleotide containing at least 15 successive nucleotides of the polynucleotide sequence of a), b) or c), the polypeptide preferably having the activity of the sigma factor C.

The present invention also provides the aforementioned polynucleotide, which is preferably a replicable DNA containing:

(i) the nucleotide sequence shown in SEQ ID No. 1, or
(ii) at least one sequence that corresponds to the sequence (i) within the region of degeneracy of the genetic code, or
(iii) at least one sequence that hybridizes with the sequence that is complementary to the sequence (i) or (ii), and optionally
(iv) functionally neutral sense mutations in (i).

The invention furthermore provides
a replicable polynucleotide, in particular DNA, containing the nucleotide sequence as shown in SEQ ID No. 1;
a polynucleotide coding for a polypeptide that contains the amino acid sequence as shown in SEQ ID No. 2;
a vector containing the polynucleotide according to the invention, in particular a shuttle vector or plasmid vector, and
coryneform bacteria that contain the vector or in which the sigC gene is enhanced.

The present invention moreover provides polynucleotides that consist substantially of a polynucleotide sequence that can be obtained by screening by means of hybridization of a corresponding gene library of a coryneform bacterium that contains the complete gene or parts thereof, with a probe that contains the sequence of the polynucleotide of the invention according to SEQ ID No. 1 or a fragment thereof, and isolation of the aforementioned polynucleotide sequence.

BRIEF DESCRIPTION OF THE FIGURES

FIG. 1: Map of the plasmid pEC-XK99E
FIG. 2: Map of the plasmid pEC-XK99EsigCb2ex The abbreviations and acronyms used have the following meanings:

| | |
|---|---|
| Kan: | Kanamycin resistence gene aph(3')-IIa from *Escherichia coli* |
| HindIII | Cleavage site of the restriction enzyme HindIII |
| XbaI | Cleavage site of the restriction enzyme XbaI |
| KpnI | Cleavage site of the restriction enzyme KpnI |
| Ptrc | trc promoter |
| T1 | Termination region T1 |
| T2 | Termination region T2 |
| Per | Replication effector per |
| Rep | Replication region rep of the plasmid pGA1 |
| LacIq | lacIq repressor of the lac operon of *Escherichia coli* |
| SigC | Cloned sigC gene |

DETAILED DESCRIPTION OF THE INVENTION

Polynucleotides that contain the sequences according to the invention are suitable as hybridization probes for RNA, cDNA and DNA in order to isolate nucleic acids or polynucleotides or genes in their full length that code for the sigma factor C, or to isolate such nucleic acids or polynucleotides or genes that have a high sequence similarity to that of the sigC genes. They are also suitable for incorporation in so-called "arrays", "micro arrays" or "DNA chips" in order to detect and determine the corresponding polynucleotides.

Polynucleotides that contain the sequences according to the invention are furthermore suitable as primers with the aid of which, and by employing the polymerase chain reaction (PCR), DNA of genes can be produced that code for the sigma factor C.

Such oligonucleotides serving as probes or primers contain at least 25, 26, 27, 28, 29 or 30, preferably at least 20, 21, 22, 23 or 24, and most particularly preferably at least 15, 16, 17, 18 or 19 successive nucleotides. Also suitable are oligonucleotides with a length of at least 31, 32, 33, 34, 35, 36, 37, 38, 39 or 40, or at least 41, 42, 43, 44, 45, 46, 47, 48, 49 or 50 nucleotides. Also suitable if necessary are oligonucleotides with a length of at least 100, 150, 200, 250 or 300 nucleotides.

"Isolated" denotes separated from its natural environment.

"Polynucleotide" refers in general to polyribonucleotides and polydeoxyribonucleotides, which may be unmodified RNA or DNA or modified RNA or DNA.

The polynucleotides according to the invention include a polynucleotide according to SEQ ID No. 1 or a fragment produced therefrom, and also polynucleotides that are at least 70% to 80%, preferably at least 81% to 85%, and particularly preferably at least 86% to 90%, and most particularly preferably at least 91%, 93%, 95%, 97% or 99% identical to the polynucleotide according to SEQ ID No. 1 or a fragment produced therefrom.

The term "polypeptides" is understood to mean peptides or proteins that contain two or more amino acids bound by peptide bonds.

The polypeptides according to the invention include a polypeptide according to SEQ ID No. 2, in particular those with the biological activity of the sigma factor C and also those that are at least 70% to 80%, preferably at least 81% to 85%, particularly preferably at least 86% to 90%, and most particularly preferably at least 91%, 93%, 95%, 97% or 99% identical to the polypeptide according to SEQ ID No. 2 and that have the aforementioned activity.

The invention furthermore provides a process for the enzymatic production of amino acids selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine, using coryneform bacteria that in particular already produce amino acids and in which the nucleotide sequences coding for the sigC gene are enhanced, in particular overexpressed.

The term "enhancement" describes in this connection the raising of the intracellular activity of one or more enzymes in a microorganism that are coded by the corresponding DNA, by for example increasing the number of copies of the gene or genes, using a strong promoter, or using a gene that codes for a corresponding enzyme having a high activity, and optionally combining these measures.

By enhancement measures, in particular overexpression, the activity or concentration of the corresponding protein is in general raised by at least 10%, 25%, 50%, 75%, 100%, 150%, 200%, 300%, 400% or 500%, at most up to 1000% or 2000%, referred to the wild type protein and/or to the activity or concentration of the protein in the starting microorganism.

The microorganisms that are the subject of the present invention are able to produce L-amino acids from glucose, sucrose, lactose, fructose, maltose, molasses, starch, cellulose or from glycerol and ethanol. The microorganisms may be representatives of coryneform bacteria, in particular of the genus *Corynebacterium*. In the genus *Corynebacterium* there should in particular be mentioned the species *Corynebacterium glutamicum*, which is known to those skilled in the art for its ability to produce L-amino acids.

Suitable strains of the genus *Corynebacterium*, in particular of the species *Corynebacterium glutamicum* (*C. glutamicum*), are in particular the known wild type strains
*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-amino acid-producing mutants or strains produced therefrom.

The inventors have successfully isolated from *C. glutamicum* the new sigC gene coding for the enzyme sigma factor C.

In order to isolate the sigC gene or also other genes from *C. glutamicum*, a gene library of this microorganism is first of all incorporated in *Escherichia coli* (*E. coli*). The incorporation of gene libraries is described in generally known textbooks and manuals. As examples there may be mentioned the textbook by Winnacker: Gene and Klone, Eine Einführung in die Gentechnologie (Verlag Chemie, Weinheim, Germany, 1990 I.B.R.) or the manual by Sambrook et al.: Molecular Cloning, A Laboratory Manual (Cold Spring Harbor Laboratory Press, 1989) I.B.R. A very well-known gene library is that of the *E. coli* K-12 strain W3110, which was incorporated by Kohara et al. (Cell 50, 495–508 (1987)) I.B.R. into λ vectors. Bathe et al. (Molecular and general genetics, 252:255–265, 1996) I.B.R. describe a gene library of *C. glutamicum* ATCC13032 that has been incorporated by means of the cosmid vector SuperCos I (Wahl et al., 1987, Proceedings of the National Academy of Sciences USA, 84:2160–2164 I.B.R.) in the *E. coli* K-12 strain NM554 (Raleigh et al., 1988, Nucleic Acids Research 16:1563–1575 I.B.R.).

Börmann et al. (Molecular Microbiology 6(3), 317-326) (1992)) I.B.R. in turn describe a gene library of *C. glutamicum* ATCC13032 using the cosmid pHC79 (Hohn and Collins, Gene 11, 291–298 (1980) I.B.R.).

In order to produce a gene library of *C. glutamicum* in *E. coli*, there may also be used plasmids such as pBR322 (Bolivar, Life Sciences, 25, 807–818 (1979) I.B.R.) or pUC9 (Vieira et al., 1982, Gene, 19:259–268 I.B.R.). Suitable hosts are in particular those *E. coli* strains that are restriction-defective and recombinant-defective. An example of such is the strain DH5αmcr, which has been described by Grant et al. (Proceedings of the National Academy of Sciences USA, 87 (1990) 4645–4649 I.B.R.). The long DNA fragments cloned with the aid of cosmids can in turn then be subcloned into common vectors suitable for the sequencing and subsequently sequenced, as is described for example by Sanger et al. (Proceedings of the National Academy of Sciences of the United States of America, 74:5463–5467, 1977 I.B.R.).

The DNA sequences obtained can then be investigated using known algorithms or sequence analysis programs, such as for example that of Staden (Nucleic Acids Research 14, 217–232(1986)) I.B.R., that of Marck (Nucleic Acids Research 16, 1829–1836 (1988)) I.B.R. or the GCG program of Butler (Methods of Biochemical Analysis 39, 74–97 (1998)) I.B.R. Analysis can also be carried out with the "BLAST search program" (Altschul et al., 1997, Nucleic Acids Research, 25:3389–3402) I.B.R., against the non-redundant databank of the "National Center for Biotechnology Information" (NCBI, Bethesda, Md., USA). The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach")", Oxford Univ. Press, Inc. (1997) I.B.R. and by Steinberg, Michael "Protein Structure Prediction" (A Practical Approach), Oxford Univ. Press, Inc. (1997) I.B.R.

The new DNA sequence of *C. glutamicum* coding for the sigC gene was obtained in this way, and as SEQ ID No. 1 is part of the present invention. The amino acid sequence of the corresponding protein was also derived from the existing DNA sequence using the afore-described methods. The resultant amino acid sequence of the sigC gene product is shown in SEQ ID No. 2.

Coding DNA sequences that result from SEQ ID No. 1 due to the degeneracy of the genetic code are likewise covered by the present invention. Similarly, DNA sequences that hybridize with SEQ ID No. 1 or parts of SEQ ID No. 1 are also part of the invention. In the specialist field conservative amino acid replacements, such as for example the replacement of glycine by alanine or of aspartic acid by glutamic acid, in proteins are furthermore known as sense mutations that do not lead to any basic change in the activity of the protein, i.e. are functionally neutral. It is furthermore known that changes at the N-end and/or C-end of a protein do not significantly impair their function or indeed may even stabilize their function. The person skilled in the art can find relevant information on this in, inter alia, Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks and manuals on genetics and molecular biology. Amino acid sequences that are obtained in a corresponding manner from SEQ ID No. 2 are likewise covered by the invention.

In the same way, DNA sequences that hybridize with SEQ ID No. 1 or parts of SEQ ID No. 1 are also covered by the invention. Finally, DNA sequences that are produced by the polymerase chain reaction (PCR) using primers resulting from SEQ ID No. 1, are also part of the invention. Such oligonucleotides typically have a length of at least 15 nucleotides.

The person skilled in the art can find information on the identification of DNA sequences by means of hybridization in, inter alia, the manual "The DIG System User's Guide for Filter Hybridization" published by Boehringer Mannheim GmbH (Mannheim, Germany, 1993) I.B.R. and in Liebl et al. (International Journal of Systematic Bacteriology (1991) 41: 255–260) I.B.R. The hybridization takes place under strict conditions, in other words only hybrids are formed in which the probe and target sequence, i.e. the polynucleotides treated with the probe, are at least 70% identical. It is known that the strictness of the hybridization conditions including the washing step is influenced or determined by varying the buffer composition, temperature and the salt concentration. The hybridization reaction is preferably carried out under conditions that are relatively less strict compared to the wash steps (Hybaid Hybridisation Guide, Hybaid Limited, Teddington, UK, 1996) I.B.R.

For the hybridization reaction there may for example be used a 5×SSC buffer at a temperature of ca. 50–68° C. In this connection probes can also hybridize with polynucleotides that are less than 70% identical to the probe sequence. Such hybrids are less stable and are removed by washing under stringent conditions. This may be achieved for example by reducing the salt concentration to 2×SSC and then if necessary to 0.5×SSC (The DIG System User's Guide for Filter Hybridisation, Boehringer Mannheim, Mannheim, Germany, 1995 I.B.R.), a temperature of ca. 50–68° C. being established. It is also possible to reduce the salt concentration down to 0.1×SSC. By stepwise raising of the hybridisation temperature in steps of ca. 1–2° C. from 50 to 68° C., polynucleotide fragments can be isolated that are for example at least 70% or at least 80% or even at least 90% to 95% identical to the sequence of the probe that is used. Further details relating to hybridisation may be obtained in the form of so-called kits available on the market (e.g. DIG Easy Hyb from Roche Diagnostics GmbH, Mannheim, Germany, Catalog No. 1603558).

The person skilled in the art can find details on the amplification of DNA sequences by means of the polymerase chain reaction (PCR) in, inter alia, the manual by Gait: Oligonucleotides Synthesis: A Practical Approach (IRL Press, Oxford, UK, 1984) I.B.R. and in Newton and Graham: PCR (Spektrum Akademischer Verlag, Heidelberg, Germany, 1994) I.B.R.

In the course of work carried in connection with the present invention it was established that coryneform bacteria after overexpression of the sigC gene produce amino acids in an improved manner.

In order to achieve an overexpression the number of copies of the corresponding genes can be increased, or alternatively the promoter and regulation region or the ribosome binding site located upstream of the structure gene can be mutated. Expression cassettes that are incorporated upstream of the structure gene act in the same way. By means of inducible promoters it is in addition possible to increase the expression in the course of the enzymatic amino acid production. The expression is similarly improved by measures aimed at prolonging the lifetime of the m-RNA.

Furthermore, the enzyme activity is also enhanced by preventing the degradation of the enzyme protein. The genes or gene constructs may either be present in plasmids having different numbers of copies, or may be integrated and amplified in the chromosome. Alternatively, an overexpression of the relevant genes may furthermore be achieved by altering the composition of the media and the culture conditions.

The person skilled in the art can find details on the above in, inter alia, Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430 (1988)) I.B.R., in Eikmanns et al. (Gene 102, 93–98 (1991)) I.B.R., in European Patent Specification 0 472 869 I.B.R., in U.S. Pat. No. 4,601,893 I.B.R., in Schwarzer and Puhler (Bio/Technology 9, 84–87 (1991) I.B.R., in Reinscheid et al. (Applied and Environmental Microbiology 60, 126–132 (1994)) I.B.R., in LaBarre et al. (Journal of Bacteriology 175, 1001–1007 (1993)) I.B.R., in Patent Application WO 96/15246 I.B.R., in Malumbres et al. (Gene 134, 15–24 (1993)) I.B.R., in Japanese laid open Specification JP-A-10-229891 I.B.R., in Jensen and Hammer (Biotechnology and Bioengineering 58, 191–195 (1998)) I.B.R., in Makrides (Microbiological Reviews 60:512–538 (1996)) I.B.R. and in known textbooks on genetics and molecular biology.

For the enhancement the sigC gene according to the invention was overexpressed for example by means of episomal plasmids. Suitable plasmids are those that are replicated in coryneform bacteria. Numerous known plasmid vectors, such as for example pZ1 (Menkel et al., Applied and Environmental Microbiology (1989) 64: 549–554 I.B.R.), pEKEx1 (Eikmanns et al., Gene 102: 93–98 (1991) I.B.R.) or pHS2-1 (Sonnen et al., Gene 107:69–74 (1991) I.B.R.) are based on the cryptic plasmids pHM1519, pBL1 or pGA1. Other plasmid vectors, such as for example those based on pCG4 (U.S. Pat. No. 4,489,160 I.B.R.), or pNG2 (Serwold-Davis et al., FEMS Microbiology Letters 66, 119–124 (1990) I.B.R.), or pAG1 (U.S. Pat. No. 5,158,891 I.B.R.) may be used in a similar way.

Furthermore, also suitable are those plasmid vectors with the aid of which the process of gene amplification by integration in the chromosome can be employed, such as has been described for example by Reinscheid et al. (Applied and Environmental Microbiology 60, 126–132 (1994) I.B.R.) for the duplication and amplification of the hom-thrB operon. In this method the complete gene is cloned into a plasmid vector that can replicate in a host (typically *E. coli*) but not in *C. glutamicum*. Suitable vectors are for example pSUP301 (Simon et al., Bio/Technology 1, 784–791 (1983) I.B.R.), pK18mob or pK19mob (Schafer et al., Gene 145, 69–73 (1994) I.B.R.), pGEM-T (Promega Corporation, Madison, Wis., USA), pCR2.1-TOPO (Shuman (1994). Journal of Biological Chemistry 269:32678–84 I.B.R.; U.S. Pat. No. 5,487,993 I.B.R.), pCR®Blunt (Invitrogen, Groningen, Netherlands; Bernard et al., Journal of Molecular Biology, 234: 534–541 (1993)) I.B.R., pEM1 (Schrumpf et al, 1991, Journal of Bacteriology 173:4510–4516 I.B.R.) or pBGS8 (Spratt et al., 1986, Gene 41: 337–342 I.B.R.). The plasmid vector that contains the gene to be amplified is then transferred by conjugation or transformation into the desired strain of *C. glutamicum*. The method of conjugation is described for example in Schafer et al. (Applied and Environmental Microbiology 60, 756–759 (1994)) I.B.R. Transformation methods are described for example in Thierbach et al. (Applied Microbiology and Biotechnology 29, 356–362 (1988)) I.B.R., Dunican and Shivnan (Bio/Technology 7, 1067–1070 (1989)) I.B.R. and Tauch et al. (FEMS Microbiological Letters 123, 343–347 (1994)) I.B.R. After homologous recombination by means of a crossover event, the resulting strain contains at least two copies of the relevant gene.

In addition it may be advantageous for the production of L-amino acids to enhance, in particular to overexpress, in addition to the sigC gene also one or more enzymes of the respective biosynthesis pathway, glycolysis, anaplerosis, citric acid cycle, pentose phosphate cycle, amino acid export and optionally regulatory proteins.

Thus for example, for the production of L-amino acids, in addition to the enhancement of the sigC gene one or more genes selected from the following group may be enhanced, in particular overexpressed:

the gene dapA coding for dihydrodipicolinate synthase (EP-B 0 197 335 I.B.R.), the gene gap coding for glyceraldehyde-3-phosphate dehydrogenase (Eikmanns (1992), Journal of Bacteriology 174:6076–6086 I.B.R.), the gene tpi coding for triosephosphate isomerase (Eikmanns (1992), Journal of Bacteriology 174:6076–6086 I.B.R.), the gene pgk coding for 3-phosphoglycerate kinase (Eikmanns (1992), Journal of Bacteriology 174:6076–6086 I.B.R.), the gene zwf coding for glucose-6-phosphate dehydrogenase (JP-A-09224661 I.B.R.), the gene pyc coding for pyruvate carboxylase (DE-A-198 31 609 I.B.R.), the gene mqo coding for malate-quinone-oxidoreductase (Molenaar et al., European Journal of Biochemistry 254, 395–403 (1998) I.B.R.), the gene lysC coding for a feedback-resistant aspartate kinase (Accession No.P26512; EP-B-0387527 I.B.R.; EP-A-0699759 I.B.R.), the gene lysE coding for lysine export (DE-A-195 48 222 I.B.R.), the gene hom coding for homoserine dehydrogenase (EP-A 0131171 I.B.R.), the gene ilvA coding for threonine dehydratase (Möckel et al., Journal of Bacteriology (1992) 8065–8072) I.B.R.) or the allele ilvA(Fbr) coding for a feedback-resistant threonine dehydratase (Möckel et al., (1994) Molecular Microbiology 13: 833–842 I.B.R.), the gene ilvBN coding for acetohydroxy acid synthase (EP-B 0356739 I.B.R.), the gene ilvD coding for dihydroxy acid dehydratase (Sahm and Eggeling (1999) Applied and Environmental Microbiology 65: 1973–1979 I.B.R.), the gene zwa1 coding for the Zwa1 protein (DE: 19959328.0 I.B.R., DSM 13115).

Furthermore, it may be advantageous for the production of L-amino acids, in addition to the enhancement of the sigC genes also to attenuate, in particular to reduce, the expression of one or more genes selected from the group the gene pck coding for phosphoenol pyruvate carboxykinase (DE 199 50 409.1 I.B.R.; DSM 13047), the gene pgi coding for glucose-6-phosphate isomerase (U.S. Pat. No. 09/396,478 I.B.R.; DSM 12969), the gene poxB coding for pyruvate oxidase (DE: 1995 1975.7; DSM 13114), the gene zwa2 coding for the Zwa2 protein (DE: 19959327.2 I.B.R., DSM 13113).

The term "attenuation" describes in this connection the reduction or switching off of the intracellular activity of one or more enzymes (proteins) in a microorganism that are coded by the corresponding DNA, by for example using a weak promoter or a gene or allele that codes for a corresponding enzyme having a low activity and/or that inactivates the corresponding gene or enzyme (protein), and optionally combining these measures.

By means of these attenuation measures the activity or concentration of the corresponding protein is in general reduced to 0 to 75%, 0 to 50%, 0 to 25%, 0 to 10% or 0 to 5% of the activity or concentration of the wild type protein and/or the activity or concentration of the protein in the starting microorganism.

In addition it may be advantageous for the production of amino acids, in addition to the overexpression of the sigC gene also to switch off undesirable secondary reactions (Nakayama: "Breeding of Amino Acid Producing Microorganisms", in: Overproduction of Microbial Products, Krumphanzl, Sikyta, Vanek (eds.), Academic Press, London, UK, 1982) I.B.R.

The microorganisms produced according to the invention are likewise the subject of the invention and may be cultivated continuously or batchwise in a batch process (batch cultivation) or in a fed batch process (feed process) or repeated fed batch process (repetitive feed process) for the purposes of production of amino acids. A summary of know cultivation methods is given in the textbook by Chmiel (Bioprozeβtechnik 1. Einführung in die Bioverfahrenstechnik (Gustav Fischer Verlag, Stuttgart, 1991)) I.B.R. or in the textbook by Storhas (Bioreaktoren und periphere Einrichtungen (Vieweg Verlag, Brunswick/Wiesbaden, 1994)) I.B.R.

The culture medium to be used must suitably satisfy the requirements of the relevant strains. Descriptions of culture media for various microorganisms are given in the manual "Manual of Methods for General Bacteriology" of the American Society for Bacteriology (Washington D.C., USA, 1981) I.B.R.

Carbon sources that may be used included sugars and carbohydrates such as for example glucose, sucrose, lactose, fructose, maltose, molasses, starch and cellulose, oils and fats such as for example soya bean oil, sunflower oil, peanut oil and coconut oil, fatty acids such as for example palmitic acid, stearic acid and linoleic acid, alcohols such as for example glycerol and ethanol, and organic acids such as for example acetic acid. These substances may be used individually or as a mixture.

Nitrogen sources that may be used include organic nitrogen-containing compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources may be used individually or as a mixture.

Phosphorus sources that may be used include phosphoric acid, potassium dihydrogen phosphate or dipotassium hydrogen phosphate or the corresponding sodium salts. The culture medium must furthermore contain salts of metals, such as for example magnesium sulfate or iron sulfate, that are necessary for growth. Finally, essential growth promoters such as amino acids and vitamins may be used in addition to the aforementioned substances. Suitable precursors may furthermore be added to the culture medium. The aforementioned starting substances may be added to the culture in the form of a single one-off batch, or may be suitably metered in during the culture process.

Basic compounds such as sodium hydroxide, potassium hydroxide, ammonia or ammonia water, or acidic compounds such as phosphoric acid or sulfuric acid, are used in a suitable manner in order to control the pH of the culture. Anti-foaming agents such as for example fatty acid polyglycol esters may be used to control foam formation. In order to maintain the stability of plasmids suitable selectively acting substances such as for example antibiotics may be added to the medium. In order to maintain aerobic conditions, oxygen or oxygen-containing gas mixtures such as for example air are introduced into the culture. The temperature of the culture is normally 20° C. to 45° C. and preferably 25° C. to 40° C. The culture is continued until a maximum of the desired product has been formed. This objective is normally achieved within 10 hours to 160 hours.

Methods for the determination of L-amino acids are known to the person skilled in the art. The analysis may be carried out for example as described by Spackman et al. (Analytical Chemistry, 30, (1958), 1190) I.B.R. by ion exchange chromatography followed by ninhydrin derivation, or can be carried out by reversed phase HPLC, as described by Lindroth et al. (Analytical Chemistry (1979) 51: 1167–1174) I.B.R.

The process according to the invention serves for the enzymatic production of amino acids.

The following microorganisms were filed as a pure culture at the German Collection of Microorganisms and Cell Cultures (DSMZ, Mascheroder Weg 1b D-38124, Brunswick, Germany) according to the Budapest Convention:

*Escherichia coli* DH5αmcr/pEC-XK99EsigCb2ex as DSM 14375 on Jun. 29, 2001

*Corynebacterium glutamicum* DSM 5715/pEC-XK99E as DMS 13455 on Apr. 17, 2000.

The present invention is described in more detail hereinafter with the aid of examples of implementation.

The isolation of plasmid DNA from *Escherichia coli* as well as all techniques involved in restriction, Klenow treatment and alkaline phosphatase treatment have been carried out by Sambrook et al. (Molecular Cloning. A Laboratory Manual (1989) Cold Spring Harbor Laboratory Press, Cold Spring Harbor, N.Y., USA) I.B.R. Methods for the transformation of *Escherichia coli* are also described in this manual.

The composition of readily available nutrient media such as LB or TY media are also given in the manual by Sambrook et al.

EXAMPLE 1

Production of a Genomic Cosmid Gene Library from *Corynebacterium Glutamicum* ATCC 13032

Chromosomal DNA from *Corynebacterium glutamicum* ATCC 13032 was isolated as described by Tauch et al. (1995, Plasmid 33:168–179 I.B.R.) and partially cleaved with the restriction enzyme Sau3AI (Amersham Pharmacia, Freiburg, Germany, product description Sau3AI, Code no. 27-0913-02). The DNA fragments were desphosphorylated with shrimp alkaline phosphatase (Roche Diagnostics GmbH, Mannheim, Germany, product description SAP, Code no. 1758250). The DNA of the cosmid vector SuperCos1 (Wahl et al. (1987) Proceedings of the National Academy of Sciences USA 84:2160–2164 I.B.R.), obtained from Stratagene (La Jolla, USA, product description SuperCos1 Cosmid Vector Kit, Code no. 251301) was cleaved with the restriction enzyme XbaI (Amersham Pharmacia, Freiburg, Germany, product description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, product description BamHI, Code no. 27-0868-04 I.B.R.). The cosmid DNA treated in this way was mixed with the treated ATCC13032-DNA and the batch was treated with T4-DNA ligase (Amersham Pharmacia, Freiburg, Germany, product description T4-DN ligase, Code no. 27-0870-04 I.B.R.). The ligation mixture was then packed into phages using the Gigapack II XL Packing Extracts (Stratagene, La Jolla, USA, product description Gigapack II XL Packing Extract, Code no. 200217 I.B.R.).

For the infection of the *E. coli* strain NM554 (Raleigh et al. 1988, Nucleic Acid Research 16:1563–1575 I.B.R.) the cells were taken up in 10 mM MgSO$_4$ and mixed with an aliquot of the phage suspension. Infection and titration of the cosmid library were carried out as described by Sambrook et al. (1989, Molecular Cloning: A Laboratory Manual, Cold Spring Harbor) I.B.R., the cells having been plated out on LB agar (Lennox, 1955, Virology, 1:190 I.B.R.) with 100 mg/l ampicillin. Recombinant individual clones were selected after incubation overnight at 37° C.

EXAMPLE 2

Isolation and Sequencing of the sigC Gene

The cosmid DNA of an individual colony was isolated using the Qiaprep Spin Miniprep Kit (Product No. 27106, Qiagen, Hilden, Germany) according to the manufacturer's instructions and partially cleaved with the restriction enzyme Sau3AI (Amersham Pharmacia, Freiburg, Germany, product description Sau3AI, Product No. 27-0913-02). The DNA fragments were dephosphorylated with shrimp alkaline phosphatase (Roche Diagnostics GmbH, Mannheim, Germany, product description SAP, Product No. 1758250). After gel electrophoresis separation, the cosmid fragments were isolated in an order of magnitude of 1500 to 2000 bp using the QiaExII Gel Extraction Kit (Product No. 20021, Qiagen, Hilden, Germany).

The DNA of the sequencing vector pZero-1, obtained from Invitrogen (Groningen, Netherlands, product description Zero Background Cloning Kit, Product No. K2500-01), was cleaved with the restriction enzyme BamHI (Amersham Pharmacia, Freiburg, Germany, product description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor I.B.R.), the DNA mixture having been incubated overnight with T4 ligase (Pharmacia Biotech, Freiburg, Germany). This ligation mixture was then electroporated (Tauch et al. 1994, FEMS Microbiol. Letters, 123:343–7 I.B.R.) into the *E. coli* strain DH5αMCR (Grant, 1990, Proceedings of the National Academy of Sciences U.S.A., 87:4645–4649 I.B.R.) and plated out onto LB agar (Lennox, 1955, Virology, 1:190 I.B.R.) with 50 mg/l zeocin.

The plasmid preparation of the recombinant clone was performed with the Biorobot 9600 (Product No. 900200, Qiagen, Hilden, Germany). The sequencing was carried out according to the dideoxy chain termination method of Sanger et al. (1977, Proceedings of the National Academy of Sciences U.S.A., 74:5463–5467 I.B.R.) as modified by Zimmermann et al. (1990, Nucleic Acids Research, 18:1067) I.B.R. The "RR dRhodamin Terminator Cycle Sequencing Kit" of PE Applied Biosystems (Product No. 403044, Weiterstadt, Germany) was used. The gel electrophoresis separation and analysis of the sequencing reaction was carried out in a "rotiphoresis NF acrylamide/bisacrylamide" gel (29:1) (Product No. A124.1, Roth, Karlsruhe, Germany) using the "ABI Prism 377" sequencing apparatus from PE Applied Biosystems (Weiterstadt, Germany).

The raw sequencing data obtained were then processed using the Staden program package (1986, Nucleic Acids Research, 14:217–231) I.B.R. Version 97-0. The individual sequences of the pzero1 derivatives were assembled into a coherent contig. The computer-assisted coding region analysis was prepared using the XNIP program (Staden, 1986, Nucleic Acids Research, 14:217–231 I.B.R.).

The nucleotide sequence obtained is shown in SEQ ID No. 1. The analysis of the nucleotide sequence revealed an open reading frame of 582 base pairs, which was termed the sigC gene. The sigC gene codes for a protein of 193 amino acids.

EXAMPLE 3

Production of the Shuttle Expression Vector pEC-XK99EsigCb2ex for the Enhancement of the sigC Gene in *C. Glutamicum*.

3.1 Cloning of the sigC Gene

Chromosomal DNA was isolated from the strain ATCC 13032 according to the method of Eikmanns et al. (Microbiology 140: 1817–1828 (1994)) I.B.R. The following oligonucleotides for the polymerase chain reaction were selected on the basis of the sequence of the sigC gene known from Example 2 for *C. glutamicum* (see SEQ ID No. 3 and SEQ ID No. 4):

```
sigCex1:
5' ac ggt acc-ccc tac aca cct tta tgg tg 3'    SEQ ID NO: 3 sigCex2:
5' gc tct aga-gtt gac gta gct cat ctg ct 3'    SEQ ID NO: 4
```

The illustrated primers were synthesised by MWG-Biotech AG (Ebersberg, Germany) and the PCR reaction was carried out according to the standard PCR method of Innis et al. (PCR protocols. A guide to methods and applications, 1990, Academic Press) I.B.R. using Pwo polymerase from Roche Diagnostics GmbH (Mannheim, Germany). With the aid of the polymerase chain reaction the primers permit the amplification of a 667 bp long DNA fragment that carries the sigC gene. Also, the primer sigCex1 carries the sequence for the cleavage site of the restriction endonuclease KpnI, and the primer sigCex2 contains the cleavage site of the restriction endonuclease XbaI, which are underlined in the nucleotide sequence illustrated above.

The 667 bp long sigC fragment was cleaved with the restriction endonucleases KpnI and XbaI and then isolated from the agarose gel using the QiaExII Gel Extraction Kit (Product No. 20021, Qiagen, Hilden, Germany).

3.2 Construction of the Shuttle Vector pEC-XK99E

The *E. coli-C. glutamicum* shuttle vector pEC-XK99E was constructed according to the prior art. The vector contains the replication region rep of the plasmid pGA1 including the replication effector per (U.S. Pat. No. 5,175, 108 I.B.R.; Nesvera et al., Journal of Bacteriology 179, 1525–1532 (1997)) I.B.R., the kanamycin resistance gene aph(3')-IIa from *Escherichia coli* (Beck et al. (1982), Gene 19: 327–336 I.B.R.), the replication origin, the trc promoter, the termination regions T1 and T2, the lacI$^q$ gene (repressor of the lac-operon of *E.coli*) and a multiple cloning site (mcs) (Norrander, J. M. et al. Gene 26, 101–106 (1983) I.B.R.) of the plasmid pTRC99A (Amann et al. (1988), Gene 69: 301–315 I.B.R.).

The trc promoter can be induced by adding the lactose derivative IPTG (isopropyl-β-D-thiogalactopyranoside).

The constructed *E. coli-C. glutamicum* shuttle vector pEC-XK99E was transferred by means of electroporation (Liebl et al., 1989, FEMS Microbiology Letters, 53:299–303 I.B.R.) into *C. glutamicum* DSM5715. The selection of the transformants was carried out on LBHIS agar consisting of 18.5 g/l brain-heart infusion broth, 0.5 M sorbitol, 5 g/l bacto-tryptone, 2.5 g/l bacto-yeast extract, 5 g/l NaCl and 18 g/l bacto-agar that had been supplemented with 25 mg/l kanamycin. Incubation was carried out for 2 days at 33° C.

Plasmid DNA was isolated from a transformant by the usual methods (Peters-Wendisch et al., 1998, Microbiology, 144, 915–927 I.B.R.), cleaved with the restriction endonuclease HindIII, and the plasmid was checked by subsequent agarose gel electrophoresis.

The plasmid construct thereby obtained was termed pEC-XK99E (FIG. 1). The strain obtained by electroporation of the plasmid pEC-XK99E into the *C. glutamicum* strain DSM5715 was identified as DSM5715/pEC-XK99E and filed as DSM13455 in the German Collection of Microorganisms and Cell Cultures (DSMZ, Brunswick, Germany) according to the Budapest Convention.

3.3 Cloning of sigC in the *E. coli-C. glutamicum* shuttle vector pEC-XK99E

The *E. coli-C. glutamicum* shuttle vector pEC-XK99E described in Example 3.2 was used as vector. DNA of this plasmid was completely cleaved with the restriction enzymes KpnI and XbaI and then dephosphorylated with shrimp alkaline phosphatase (Roche Diagnostics GmbH, Mannheim, Germany, product description SAP, Product No. 1758250 I.B.R.).

The ca. 650 bp long sigC fragment described in Example 3.1, which was obtained by PCR and cleaved with the restriction endonucleases KpnI and XbaI, was mixed with the prepared vector pEC-XK99E and the batch was treated with T4-DNA ligase (Amersham Pharmacia, Freiburg, Germany, product description T4-DNA ligase, Code no. 27-0870-04 I.B.R.). The ligation batch was transformed into the *E. coli* strain DH5αmcr (Hanahan, In: DNA cloning. A practical approach. Vol. I. IRL-Press, Oxford, Washington D.C., USA I.B.R.). The selection of plasmid-carrying cells was made by plating out the transformation batch on LB agar (Lennox, 1955, Virology, 1:190 I.B.R.) with 50 mg/l kanamycin. After incubation overnight at 37° C. recombinant individual clones were selected. Plasmid DNA was isolated from a transformant using the Qiaprep Spin Miniprep Kit (Product No. 27106, Qiagen, Hilden, Germany) according to the manufacturer's instructions and cleaved with the restriction enzymes XbaI and KpnI in order to check the plasmid by subsequent agarose gel electrophoresis. The plasmid obtained was named pEC-XK99EsigCb2ex, and is shown in FIG. 2.

EXAMPLE 4

Transformation of the Strain DSM5715 with the Plasmid pEC-XK99EsigCb2ex

The strain DSM5715 was transformed with the plasmid pEC-XK99EsigCb2ex using the electroporation method described by Liebl et al., (FEMS Microbiology Letters, 53:299–303 (1989)) I.B.R. The selection of the transformants was carried out on LBHIS agar consisting of 18.5 g/l brain-heart infusion broth, 0.5 M sorbitol, 5 g/l bacto-tryptone, 2.5 g/l bacto-yeast extract, 5 g/l NaCl and 18 g/l bacto-agar that had been supplemented with 25 mg/l kanamycin. Incubation was carried out for 2 days at 33° C.

Plasmid DNA was isolated from a transformant by the usual methods (Peters-Wendisch et al., 1998, Microbiology, 144, 915–927 I.B.R.), cleaved with the restriction endonucleases XbaI and KpnI, and the plasmid was checked by subsequent agarose gel electrophoresis. The strain obtained was named DSM5715/pEC-XK99EsigCb2ex1.

EXAMPLE 5

Production of Lysine

The *C. glutamicum* strain DSM5715/pEC-XK99EsigCb2ex obtained in Example 4 was cultivated in a nutrient medium suitable for the production of lysine and the lysine concentration in the culture supernatant was determined.

For this purpose the strain was first of all incubated on an agar plate with the corresponding antibiotic (brain-heart agar with kanamycin (25 mg/l)) for 24 hours at 33° C. A pre-culture was inoculated starting from this agar plate culture (10 ml medium in a 100 ml Erlenmeyer flask). The full medium CgIII was used as medium for the pre-culture.

| Medium Cg III | |
|---|---|
| NaCl | 2.5 g/l |
| Bacto-Peptone | 10 g/l |
| Bacto-Yeast Extract | 10 g/l |
| Glucose (separately autoclaved) | 2% (w/v) |
| The pH value was adjusted to pH 7.4 | |

Kanamycin (25 mg/l) was added to the medium. The pre-culture was incubated for 16 hours at 33° C. and at 240 rpm on a shaker mixer. A main culture was inoculated from this pre-culture so that the initial OD (660 nm) of the main culture was 0.1. The medium MM was used for the main culture.

| Medium MM | |
|---|---|
| CSL (corn steep liquor) | 5 g/l |
| MOPS (morpholinopropanesulfonic acid) | 20 g/l |
| Glucose (separately autoclaved) | 50 g/l |
| $(NH_4)_2SO_4$ | 25 g/l |
| $KH_2PO_4$ | 0.1 g/l |
| $MgSO_4 \cdot 7 H_2O$ | 1.0 g/l |
| $CaCl_2 \cdot 2 H_2O$ | 10 mg/l |

| -continued | |
|---|---|
| Medium MM | |
| $FeSO_4 \cdot 7 H_2O$ | 10 mg/l |
| $MnSO_4 \cdot H_2O$ | 5.0 mg/l |
| Biotin (sterile filtered) | 0.3 mg/l |
| Thiamine · HCl (sterile filtered) | 0.2 mg/l |
| L-leucine (sterile filtered) | 0.1 g/l |
| $CaCO_3$ | 25 g/l |

CSL, MOPS and the salt solution were adjusted to pH 7 with ammonia water and autoclaved. The sterile substrate and vitamin solutions as well as the dry autoclaved $CaCO_3$ were then added.

The cultivation was carried out in 10 ml volume batches in a 100 ml Erlenmeyer flask equipped with baffles. Kanamycin (25 mg/l) and IPTG (1 mM/l) were added. The cultivation was carried out at 33° C. and 80% atmospheric humidity.

After 48 hours the OD was measured at a measurement wavelength of 660 nm using a Biomek 1000 (Beckmann Instruments GmbH, Munich). The amount of lysine formed was determined using an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | Lysine-HCl g/l |
|---|---|---|
| DSM5715 | 11.8 | 12.99 |
| DSM5715/pEC-XK99EsigCb2ex | 12.8 | 13.96 |

This application claims priority to German Priority Document Application No. 100 43 332.4, filed on Sep. 2, 2000 and to German Priority Document Application No. 101 33 426.5, filed on Jul. 10, 2001. Both German Priority Documents are hereby incorporated by reference in their entirety.

We claim:

1. A method for the production of L-amino acids using coryneform bacteria comprising:
fermenting coryneform bacteria, which produce a desired L-amino acid, comprising an overexpressed sigC polynucleotide wherein said polynucleotide encodes a polypeptide comprising the amino acid sequence of SEQ ID NO: 2, wherein overexpression is achieved by increasing the copy number of said polynucleotide or by operably linking said polynucleotide to a promoter.

2. The method according to claim 1 wherein said polynucleotide comprises nucleotides 300 to 878 of SEQ ID:1.

3. The method according to claim 1, further comprising: isolating the L-amino acid.

4. The method according to claim 1 wherein the L amino acid is lysine.

5. The method as claimed in claim 1, wherein the bacteria being fermented comprise, at the same time, one or more *Corynebacterium glutamicum* genes which are overexpressed, wherein the one or more genes is/are selected from the group consisting of:

the dapA gene coding for dihydrodipicolinate synthase,
the gap gene coding for glyceraldehyde-3-phosphate dehydrogenase,
the tpi gene coding for triosephosphate isomerase,
the pgk gene coding for 3-phosphoglycerate kinase,
the zwf gene coding for glucose-6-phosphate dehydrogenase,
the pyc gene coding for pyruvate carboxylase,
the mqo gene coding for malate quinone oxidoreductase,
the lysC gene coding for feed-back resistant aspartate kinase,
the lysE gene coding for lysine export protein,
the hom gene coding for homoserine dehydrogenase,
the ilvA gene coding for threonine dehydratase or the ilvA(Fbr) allele coding for feed-back resistant threonine dehydratase,
the ilvBN gene coding for acetohydroxy acid synthase,
the ilvD gene coding for dihydroxy acid hydratase, and
the zwa1 gene coding for the Zwa1 protein.

6. The method as claimed in claim 1, wherein the bacteria being fermented are *Corynebacterium glutamicum* and comprise, at the same time, one or more endogenous *Coryne-*

*bacterium glutamicum* genes which are eliminated, wherein the one or more genes is/are selected from the group consisting of:

the pck gene coding for phosphoenol pyruvate,
the pgi gene coding for glucose-6-phosphate isomerase,
the poxB gene coding for pyruvate oxidase, and
the zwa2 gene coding for the Zwa2 protein.

7. The method according to claim 1, wherein the bacteria is *Corynebacterium glutamicum*.

8. A method for the production of L-amino acids using coryneform bacteria comprising:

fermenting coryneform bacteria, which produce a desired L-amino acid, comprising an overexpressed sigC polynucleotide wherein said polynucleotide comprises the nucleotide sequence of SEQ ID NO:1, wherein overexpression is achieved by increasing the copy number of said polynucleotide or by operably linking said polynucleotide to a promoter.

9. The method according to claim 8, further comprising: isolating the L-amino acid.

10. The method according to claim 8, wherein the L amino acid is lysine.

11. The method as claimed in claim 8, wherein the bacteria being fermented comprise, at the same time, one or more *Corynebacterium glutamicum* genes which are overexpressed, wherein the one or more genes is/are selected from the group consisting of:

the dapA gene coding for dihydrodipicolinate synthase,
the gap gene coding for glyceraldehyde-3-phosphate dehydrogenase,
the tpi gene coding for triose phosphate isomerase,
the pgk gene coding for 3-phosphoglycerate kinase,
the zwf gene coding for glucose-6-phosphate dehydrogenase,
the pyc gene coding for pyruvate carboxylase,
the mqo gene coding for malate quinone oxidoreductase,
the lysC gene coding for feed-back resistant aspartate kinase,
the lysE gene coding for lysine export protein,
the hom gene coding for homoserine dehydrogenase,
the ilvA gene coding for threonine dehydratase or the ilvA(Fbr) allele coding for feed-back resistant threonine dehydratase,
the ilvBN gene coding for acetohydroxy acid synthase,
the ilvD gene coding for dihydroxy acid hydratase, and
the zwa1 gene coding for the Zwa1 protein.

12. The method as claimed in claim 8, wherein the bacteria being fermented are *Corynebacterium glutamicum* and comprise, at the same time, one or more endogenous *Corynebacterium glutamicum* genes which are eliminated, wherein the one or more genes is/are selected from the group consisting of:

the pck gene coding for phosphoenol pyruvate,
the pgi gene coding for glucose-6-phosphate isomerase,
the poxB gene coding for pyruvate oxidase, and
the zwa2 gene coding for the Zwa2 protein.

13. The method according to claim 8 wherein the bacteria is *Corynebacterium glutamicum*.

14. The method according to claim 8, wherein said vector is pEC-XK99EsigCb2ex contained in *Escherichia coli* strain DH5mcr/pEC-XK99EsigCb2ex deposited under DSM 14375.

15. *Corynebacterium glutamicum* DSM5715/pEC-XK99E deposited under DSM 13455.

* * * * *

SEQUENCE LISTING

<160> NUMBER OF SEQ ID NOS: 4

<210> SEQ ID NO 1
<211> LENGTH: 1109
<212> TYPE: DNA
<213> ORGANISM: Corynebacterium glutamicum
<220> FEATURE:
<221> NAME/KEY: CDS
<222> LOCATION: (300)..(878)
<223> OTHER INFORMATION:

<400> SEQUENCE: 1

```
tggaactggt gctccgttgt ggcgggtagt gtttccagaa agctttggac gcattccgcg      60
atctacgatc tggtctgctg ctgacttctc agacattagc attccttcct tttatgaggg     120
ttacctatgg attaagtctg attgatagtc tacatcagaa tgtcacttcg cgccaccaaa     180
taatcagccc ttacgtaaac tgccagcaaa aagacaaaag tatgatactt tttgcccact     240
```

-continued

```
ttgacacccc ctacacacct ttatggtgac cccggtctga actggtattc tgagcaatt      299 gtg aag tca aaa gag cgt aac gac gcc cac gtc acc gag ctg gcc cta      347
Met Lys Ser Lys Glu Arg Asn Asp Ala His Val Thr Glu Leu Ala Leu
1               5                   10                  15 gcc gcc ggc cgt ggc gac cgc gca gct ctc acc gat ttc atc cgg gaa      395
Ala Ala Gly Arg Gly Asp Arg Ala Ala Leu Thr Asp Phe Ile Arg Glu
            20                  25                  30 acc caa gac gat gtc tgg cgt ctc ctc gcc cac ctt ggc ggc cac gaa      443
Thr Gln Asp Asp Val Trp Arg Leu Leu Ala His Leu Gly Gly His Glu
        35                  40                  45 atc gcc gac gat cta acc caa gaa act tat ctg cgg gtc atg agc gcc      491
Ile Ala Asp Asp Leu Thr Gln Glu Thr Tyr Leu Arg Val Met Ser Ala
50                  55                  60 ctc ccc cgc ttc gca gcg cgc tcc tcg gcg cgt acc tgg cta cta tcg      539
Leu Pro Arg Phe Ala Ala Arg Ser Ser Ala Arg Thr Trp Leu Leu Ser
65                  70                  75                  80 cta gcc cgg cgc gtc tgg gtc gac aac atc cga cac gac atg gca cgc      587
Leu Ala Arg Arg Val Trp Val Asp Asn Ile Arg His Asp Met Ala Arg
                85                  90                  95 ccc cgc aaa tcc atc gtc gaa tac gaa gac acc ggt gcc acc gac gcg      635
Pro Arg Lys Ser Ile Val Glu Tyr Glu Asp Thr Gly Ala Thr Asp Ala
            100                 105                 110 agc aac gca ggc atc tgg tcc gag tgg atc gac gtg cgc acg ctt atc      683
Ser Asn Ala Gly Ile Trp Ser Glu Trp Ile Asp Val Arg Thr Leu Ile
        115                 120                 125 gac gcc ctc cca ccc gaa cgc cgc gaa gcc ctc atc ctc acc caa gtg      731
Asp Ala Leu Pro Pro Glu Arg Arg Glu Ala Leu Ile Leu Thr Gln Val
130                 135                 140 ttg ggc tac acc tac gaa gaa gcc gca aaa atc gcc gac gtc cga gtc      779
Leu Gly Tyr Thr Tyr Glu Glu Ala Ala Lys Ile Ala Asp Val Arg Val
145                 150                 155                 160 gga aca atc cgt tcc cgc gta gcc cgc gcc aga gcg gac ctc att gct      827
Gly Thr Ile Arg Ser Arg Val Ala Arg Ala Arg Ala Asp Leu Ile Ala
                165                 170                 175 gca aca gct acc ggt gat tcc tca gcc gaa gat ggc aaa tcc gcc caa      875
Ala Thr Ala Thr Gly Asp Ser Ser Ala Glu Asp Gly Lys Ser Ala Gln
            180                 185                 190 ggt tagcagatga gctacgtcaa cggcgtaatc ccttaaccag attgctaatt            928
Gly tacagttcta ttttgctgct cgatcaaagc gactcttacc cacctagaa tcctttgacc      988 gcatcaacac tttgttttta tctaaaactg aatctttaat ttttacgctc gcagatgatt   1048
ttcctccagc aatggaagta ataaccccgc cccgaacgac agctcttcga ggtgcgcttc   1108
c                                                                 1109
```

<210> SEQ ID NO 2
<211> LENGTH: 193
<212> TYPE: PRT
<213> ORGANISM: Corynebacterium glutamicum

<400> SEQUENCE: 2

```
Met Lys Ser Lys Glu Arg Asn Asp Ala His Val Thr Glu Leu Ala Leu
1               5                   10                  15

Ala Ala Gly Arg Gly Asp Arg Ala Ala Leu Thr Asp Phe Ile Arg Glu
            20                  25                  30

Thr Gln Asp Asp Val Trp Arg Leu Leu Ala His Leu Gly Gly His Glu
        35                  40                  45
```

-continued

```
Ile Ala Asp Asp Leu Thr Gln Glu Thr Tyr Leu Arg Val Met Ser Ala
         50                  55                  60

Leu Pro Arg Phe Ala Ala Arg Ser Ser Ala Arg Thr Trp Leu Leu Ser
65                  70                  75                  80

Leu Ala Arg Arg Val Trp Val Asp Asn Ile Arg His Asp Met Ala Arg
                 85                  90                  95

Pro Arg Lys Ser Ile Val Glu Tyr Glu Asp Thr Gly Ala Thr Asp Ala
             100                 105                 110

Ser Asn Ala Gly Ile Trp Ser Glu Trp Ile Asp Val Arg Thr Leu Ile
         115                 120                 125

Asp Ala Leu Pro Pro Glu Arg Arg Glu Ala Leu Ile Leu Thr Gln Val
     130                 135                 140

Leu Gly Tyr Thr Tyr Glu Ala Ala Lys Ile Ala Asp Val Arg Val
145                 150                 155                 160

Gly Thr Ile Arg Ser Arg Val Ala Arg Ala Arg Ala Asp Leu Ile Ala
                 165                 170                 175

Ala Thr Ala Thr Gly Asp Ser Ser Ala Glu Asp Gly Lys Ser Ala Gln
             180                 185                 190

Gly

<210> SEQ ID NO 3
<211> LENGTH: 28
<212> TYPE: DNA
<213> ORGANISM: Corynebacterium glutamicum

<400> SEQUENCE: 3
acggtacccc ctacacacct ttatggtg                                    28

<210> SEQ ID NO 4
<211> LENGTH: 28
<212> TYPE: DNA
<213> ORGANISM: Corynebacterium glutamicum

<400> SEQUENCE: 4
gctctagagt tgacgtagct catctgct                                    28
```